(12) United States Patent
Dash et al.

(10) Patent No.: US 10,368,755 B2
(45) Date of Patent: Aug. 6, 2019

(54) APPARATUS AND METHOD FOR FEATURE EXTRACTION AND CLASSIFICATION OF FETAL HEART RATE

(71) Applicant: The Research Foundation for The State University of New York, Albany, NY (US)

(72) Inventors: Shishir Dash, Port Jefferson, NY (US); J. Gerald Quirk, Saint James, NY (US); Petar Djuric, Setauket, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 0 days.

(21) Appl. No.: 15/824,215

(22) Filed: Nov. 28, 2017

(65) Prior Publication Data

US 2018/0078160 A1 Mar. 22, 2018

Related U.S. Application Data

(63) Continuation of application No. 14/314,918, filed on Jun. 25, 2014, now abandoned.

(60) Provisional application No. 61/987,628, filed on May 2, 2014, provisional application No. 61/839,077, filed on Jun. 25, 2013.

(51) Int. Cl.
*A61B 5/024* (2006.01)
*A61B 5/03* (2006.01)

(52) U.S. Cl.
CPC .......... *A61B 5/02411* (2013.01); *A61B 5/033* (2013.01)

(58) Field of Classification Search
CPC ............................ A61B 5/02411; A61B 5/033
See application file for complete search history.

(56) References Cited

U.S. PATENT DOCUMENTS

| | | | |
|---|---|---|---|
| 5,419,322 | A | 5/1995 | Joseph et al. |
| 5,609,156 | A | 3/1997 | Keith |
| 7,949,389 | B2 | 5/2011 | Wolfberg et al. |
| 2010/0041046 | A1 | 2/2010 | Chiu et al. |
| 2013/0158366 | A1 | 6/2013 | Bogineni et al. |

FOREIGN PATENT DOCUMENTS

| | | |
|---|---|---|
| WO | WO-2010/144249 | 12/2010 |
| WO | WO-2014/021515 | 2/2014 |

OTHER PUBLICATIONS

Shishir Dash et al., Classification of Fetal Heart Rates, Department of Electrical and Computer Engineering, Stony Brook University, NY. (pp. 5).

Shishir Dash et al., Learning dependencies among fetal heart rate features using Bayesian networks, Department of Electrical and Computer Engineering, Stony Brook University NY. (pp. 4).

(Continued)

*Primary Examiner* — Mark Bockleman
(74) *Attorney, Agent, or Firm* — The Farrell Law Firm, P.C.; John F. Gallagher, III

(57) ABSTRACT

Provided are a device and method for receiving a fetal heart rate (FHR) signal at each interval during a monitoring period, receiving a uterine pressure (UP) signal at each of the intervals to obtain a plurality of FHR-UP signal pairs, and extracting a feature value for each FHR-UP signal pair, with the feature value being extracted from a predefined alphabet of feature values.

10 Claims, 1 Drawing Sheet

(56) References Cited

OTHER PUBLICATIONS

Rik Vullings et al., Novel Bayesian Vectorcardiographic Loop Alignment for Improved Monitoring of ECG and Fetal Movement, IEEE Transactions on Biodmedical Engineering, vol. 60, No. 6, Jun. 2013 (pp. 9).

Shishir Dash et al., A novel clinical decision support system for analysis of fetal heart rate and maternal uterine pressure signals based on generative models, Department of Electrical and Computer Engineering, Stony Brook University, NY, May 2013. (pp. 29).

Diogo Ayres-de-Campos, Sis Porto 2.0: A Program for Automated Analysis of Cariotocograms, The Journal of Maternal-Fetal Medicine 9:311-318, Wiley-Liss, Inc. 2000 (pp. 8).

NICE Clinical guideline 55, Intrapartum care, Care of healthy women and their babies during childbirth,National Instittute for Health and Clinical Excellence, 2007. (pp. 69).

Shiying Dong et al., "Detection of Perinatal Hypoxia Using Time-Frequency Analysis of Heart Rate Variability Signals", ICASSP 2013, ResearchGate, Oct. 2013, (pp. 6).

J. Spilka et al., "J7 Using Nonlinear Features for Fetal Heart Rate Classification", ResearchGate, Nov. 2012, (pp. 17).

Elliott C. et al., "Graded Classification of Fetal Heart Rate Tracings: Association with Neonatal Metabolic Acidosis and Neurologic Morbidity", Obstetrics, American Journal of Obstetrics & Gynecology, Mar. 2010, (pp. 8).

APPARATUS AND METHOD FOR FEATURE EXTRACTION AND CLASSIFICATION OF FETAL HEART RATE

PRIORITY

This is a Continuation application of U.S. patent application Ser. No. 14/314,918 filed with the U.S. patent and Trademark Office on Jun. 25, 2014, which claims priority to Provisional Patent Applications No. 61/839,077 and 61/987,628, filed with the U.S. Patent and Trademark Office on Jun. 25, 2013 and May 2, 2014, respectively, the contents of each of which are incorporated herein by reference.

BACKGROUND OF THE INVENTION

1. Field of the Invention

The present invention generally relates to non-invasive methods and an apparatus for detection and monitoring of fetal health and, more particularly, to methods for monitoring fetal heart rate during intrapartum.

2. Description of the Related Art

Uterine contractions cause reduction in uterine and placental blood flow. Consequently, oxygen exchange through the placenta is temporarily decreased, followed by normalization of the perfusion after relaxation of the uterus. Oxygenation of the fetus is directly dependent on four factors: maternal blood pressure, maternal oxygenation, available placental surface area for perfusion, and whether the umbilical cord is sufficiently open and unobstructed. Compromise of any factor will compromise oxygen transfer and cause uteroplacental oxygen insufficiency.

During contractions, the fetus relies on appropriate residual perfusion of both maternal and fetal blood across the intervillous space, i.e., placental reserve, for oxygen supply. Uteroplacental oxygen insufficiency can occur due to an infarction in the placenta that will result in poor oxygen transfer during relaxation of the uterus, resulting in low oxygen levels, i.e., fetal hypoxemia. Alternatively, very deep contractions or an excess number of contractions per unit time will cause the placenta to not have sufficient time to absorb oxygen from maternal blood between contractions. Another cause of uteroplacental oxygen insufficiency is decreased maternal perfusion of the placenta that may occur if the mother is hypotensive, hypoxic, or has other complications. Even for contractions of normal length and size, the fetus may undergo distress because the fetus cannot absorb enough oxygen even after the contraction. A further cause of uteroplacental oxygen insufficiency occurs with umbilical cord constriction, which decreases oxygen delivery to the fetus.

Oxygenation levels in the fetal heart have a direct effect on the functioning of the fetal brain and nervous system. Since cardiac contractions in the fetal heart are regulated by the autonomic nervous system, as in adults, cardiac contractions have a direct effect on cardiovascular functioning. Accordingly, intrapartum, i.e., close to delivery, fetal heart rate (FHR) monitoring is critical since a change in oxygen level directly affects the autonomic nervous system, and therefore affects the FHR.

Conventional fetal monitors typically measure the FHR signal and maternal uterine activity, either externally or internally. Internal monitoring of the fetal heart is achieved via direct acquisition of electrocardiogram (ECG) data. In internal monitoring, the FHR is derived from the ECG signal, which has distinct morphological features in each heart beat called fiducial points, denoted the P wave, QRS complex, and the T and U waves. The R peak in the QRS complex is the most distinct and easiest to detect. The time interval between successive R peaks is called the RR interval, with the inverse called instantaneous heart rate.

In external fetal monitoring, ultrasound waves are used to detect the rhythmic movement of fetal heart valves and pulsatile blood flow via Doppler frequency shifts. A transducer that emits ultrasound waves and a sensor that detects reflected waves are placed on the maternal abdomen with a coupling gel to receive reflected waves from different moving sources, which creates a spectrum of many different frequency shifts corresponding to many different velocities, with the velocity spectrum repeated with each heart beat. An autocorrelation method is used to detect periodicity in the spectrum. In conventional Doppler fetal monitoring units, significant post-processing is done on the signal after acquisition to eliminate noise. The autocorrelation process requires at least several heartbeats to obtain data for accurate rhythmic detection, and an implicit smoothing can obscure certain high-frequency variations.

Despite the problems associated with Doppler monitoring, it is the preferred choice of obstetric care providers for FHR monitoring, with scalp-electrodes used only when warranted by necessity, such as when a cleaner signal is required for more detailed study.

To internally monitor uterine activity, a plastic, fluid filled catheter is inserted into the uterus along one side of the fetal head. The catheter is connected to a strain-gauge pressure sensor calibrated to the same level as the catheter tip in the uterus. Pressure variation within the fluid system, caused by contraction activity in the uterus, creates a potential difference that is amplified and measured as a percentage signal. To externally monitor uterine activity, a displacement transducer, typically formed as a button or plunger, is held against the abdominal wall. Each contraction moves of the plunger in proportion to the contraction strength, thereby creating a measurable electrical signal relative to contraction intensity, typically used to measure contraction onset, contraction peak and contraction return.

Conventional methods for analysis of FHR and uterine pressure patterns generally rely on parametric approaches and use summary features obtained from long stretches of data, which fail to account for local nonlinearities and nonstationarity, and are not effective in many applications, in particular for monitoring FHR during intrapartum.

SUMMARY OF THE INVENTION

The present invention overcomes the above-describes short-comings of conventional systems by providing a device and method for inputting, to a processor of the device, a fetal heart rate (FHR); inputting, to the processor, a plurality of uterine pressure (UP) values corresponding to the input FHR; removing, by the processor, artifacts from the FHR and interpolating segments of the FHR; storing, by a feature extractor, time information of segments of the interpolated FHR segments; searching sub-segments of the stored time information to detect variability of the FHR; detecting excess noise in the searched sub-segments; obtaining a reduced noise FHR signal by removing the sub-segments with detected excess noise; detecting a plurality of sub-segments of the reduced noise FHR signal corresponding to an average heart rate baseline; detecting at least two sub-segments of the plurality of sub-segments of the reduced noise FHR signal corresponding to contractions based the input plurality of UP values; and indexing each sub-segment of the detected at least two sub-segments.

BRIEF DESCRIPTION OF THE DRAWINGS

The above and other aspects, features and advantages of certain embodiments of the present invention will be more apparent from the following detailed description taken in conjunction with the accompanying drawings, in which.

DETAILED DESCRIPTION OF THE PREFERRED EMBODIMENTS

The following detailed description of certain embodiments of the present invention will be made with reference to the accompanying drawings. In describing the invention, explanation of related functions or constructions known in the art are omitted for the sake of clearness in understanding the concept of the invention, to avoid obscuring the invention with unnecessary detail.

Figure 1:
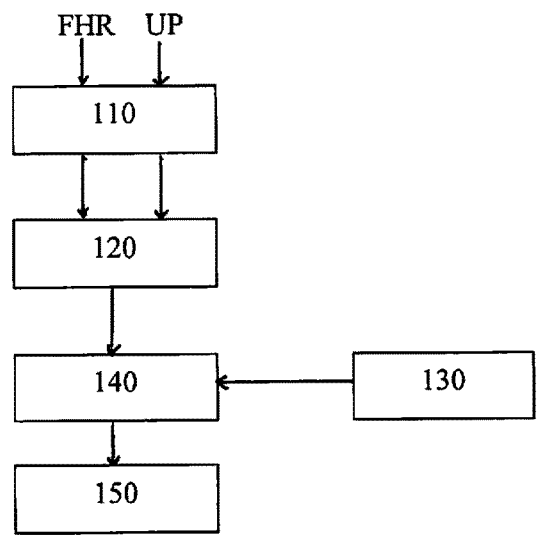
FIG. 1 is a block diagram illustrating components of an apparatus for feature extraction and classification of FHR according to an embodiment of the present invention.

FIG. 1 shows an apparatus for feature extraction and classification of fetal heart rate including a scale with a range between 0 and 100, then estimating a baseline via mode estimation. The UP signal is generally a clean signal, smoothed by an averaging filter having a fixed sample length, e.g., a length of seventeen samples. For extraction by feature extractor 120, a Gaussian kernel method is preferably used to estimate the probability mass function (pmf) using bins centered at $\{0.5, 1.5, \ldots, 99.5\}$, with kernel widths calculated using Equation 1:

Kernel width $S=0.9 \min\{\sigma, 1.4826 M_u\}$,

Where, $u=\{u[1], \ldots, u[N\, f_s]\}$, $\sigma^2$=Variance of $u$, $M_u$=Mean absolute deviation of $u$.  (1)

where u[n] is a UP signal at time instant n, N=20 minutes, with $\sigma$ being the standard deviation of the UP time series under consideration, with the square of $\sigma$ being the variance statistic that is used as a heuristic guide to decide the Gaussian kernel width for mode estimation.

The u value at which the pmf is maximized is considered baseline $b_u$. Onset of uterine contraction is detected whenever u[n] exceeds $b_u$ by a minimum of $\theta_n^u=3\%$, with that time instant denoted by $n_s^u$. For each such onset candidate, a return time $n_r^u$ is detected. If duration of contraction $L_u=(n_r^u-n_s^u)$ exceeds threshold $\theta_L^u=185\, f_u$, the mode for the candidate period is recalculated utilizing the above procedure. Onset and return detections are recursively performed until a valid contraction, if any, is detected. Once a valid contraction is detected, peak time of the contraction is $n_p^u$. For diagnosis, the contraction frequency $F_u$, defined as the number of detected contractions in a twenty minute period, is calculated as a feature of interest.

Preprocessing can be performed on input FHR before feature extraction to remove various artifacts, e.g., movement artifacts. Preprocessing is typically performed on an FHR time series acquired via Doppler-autocorrelation or internal scalp-electrode method, to remove spiky artifacts. Upon detection of FHR segments with successive HR differences greater than twenty-five beats per minute (bpm), linear interpolation is performed between the first detection and the first subsequent stable segment, i.e., a group of five samples with beat-to-beat difference not exceeding ten bpm. See, D. Ayres-de Campos, et al., *SisPorto 2.0: A Program for Automated Analysis of Cardiotocograms*, The Journal of Maternal-Fetal Medicine, 9(5):311-318, 2000).

Feature extractor 110 stores time information of interpolated segments to isolate tracing areas with large amounts of noise. To detect a deceleration/acceleration/variability FHR feature, sub-segments of an epoch are searched, with the epoch having a defined duration, e.g., twenty minutes. If a total duration of interpolated periods during any sub-segment exceeds thirty percent of the sub-segment duration, the sub-segment is rejected from the search.

Baseline is clinically defined as average heart rate over FHR periods free from episodic deviations such as accelerations, decelerations and marked variability-periods. However, episodic deviations are defined with reference to a pre-calculated baseline FHR, which leads to a problem in conventional baseline definition. Accordingly, feature extractor 110 utilizes a programmatic baseline estimation description.

Feature extractor 110 estimates baseline FHR using a windowed median filtering method with a five minute window length found appropriate for accurate baseline estimation, providing a sufficiently short window to include important slow changes in FHR trends of periods free of episodes, while rejecting shorter episode-related deviations. The baseline signal is denoted over a same time interval.

Accelerations are visually apparent abrupt increases from the baseline. Once feature extractor 110 estimates baseline FHR, the onset times of accelerations are detected as the first sample indices $n_s^A$ when the FHR h[n] upwardly deviates from $b_h[n]$ by at least $\theta_s^A=1$ bpm. For each onset candidate, return time $n_r^A$ and duration $L_A=n_r^A-n_s^A$ are estimated. If $L_A>\theta_L^A(=15\, f_s)$, location $n_p^A$ of the peak deviation from baseline, which is denoted $\bar{h}_p^A$, is estimated. Since the FHR is typically not a smooth signal, detecting an obvious peak is difficult. Hence, only a first significant peak, which is the first local maximum within a top twentieth percentile of the series of FHR deviations during acceleration. If there is no such local maximum, a global maximum is calculated during the acceleration duration. The candidate acceleration is determined to be valid upon satisfying the conditions of Equation 2:

$n_p^A-n_n^A<\theta_p^A=30\, f_s$, $\bar{h}_p^A>\theta_h^A=15$ bpm, $L_A\in[15\, f_s, 600\, f_s]$.  (2)

Decelerations are abrupt or gradual decreases from the baseline. Once feature extractor 110 estimates the baseline FHR, onset times of decelerations are detected as the first sample indices $n_s^D$ when the FHR h[n] downwardly deviates from $b_h[n]$ by at least $\theta_n^D=1$ bpm. For each onset candidate, a return time $n_r^D$ is estimated with durations $L_D=n_r^D-n_s^D$. If $L_D>\theta_L^D\,(=15\, f_s)$, it is considered a likely deceleration candidate, and nadir $n_p^D$ and the corresponding deviation from the baseline $\bar{h}_p^D$ at the nadir location are then found. In order to detect only the first significant nadir, a procedure similar to the above procedure for detection of accelerations is used. Deceleration detection is prone to false positives due to a higher degree of noise due to electrode movement/dropoff. In such instances, the signal suddenly dips below threshold, requiring time to return to baseline, artificially increasing episode abruptness. Episode abruptness is overcome by utilizing threshold $\theta_p^D=3 f_s$, to differentiate true decelerations from false episodes, with candidate deceleration having to take at least three seconds from onset to nadir to qualify as a valid deceleration.

FHR signal variability is an important feature for detection of fetal distress. Despite the literature regarding adult heart rate variability and standards of measurement, agreement does not exist for FHR studies, which beat-to-beat variability and long-term variability conventionally being visually determined as a unit. To overcome this shortcoming of conventional methods, feature extractor 110 utilizes a zero-crossing method that initially finds sub-segments in an FHR series $h=\{h[1], \ldots, h\{Nfs\}\}$ which are free of accelerations, decelerations and noise. Each such sub-segment is de-baselined using a corresponding $b_h$ value and divided into non-overlapping one-minute segments. A resulting signal $\bar{h}_u[n]$ is utilized to estimate a number of times that the signal went above, resp. below, thresholds $\theta_S$ (resp. $-\theta_S$), with the result denoted $k_v$, taken as an estimate of a number of FHR cycles around the baseline. If the per minute cycle frequency ($=k_v$) exceeds a clinical threshold, e.g., two cycles/min, for a valid variability signal, the feature of interest is estimated as follows. For each detected cycle, a crest-to-trough range is estimated with a median of these values being variability $\hat{V}_h$ for a one-minute sub-segment. To calculate a variability value for the full twenty minute signal, the median value of all the $\hat{V}_h$'s over that period is calculated, denoted $V_h$.

The extracted features, including FHR deceleration, FHR baseline and baseline variability, are input into feature symbolizer 120 for segmentation and feature discretization by addition of time information. Feature symbolizer 120 segments a dataset of an FHR-UP time series being considered, to extract sequences of feature values indicative of the morphological changes, and performs subsequent discretization of the features into a finite-sized feature value alphabet. The discretization enables efficient modeling of feature sequences using multinomial distributions, which simplifies parameter update and inference. Feature symbolizer 120 performs a variability calculation upon determination that a considered segment is suitable for the variability calculation. If the considered segment is not suitable for the variability calculation, feature symbolizer 120 identifies an acceleration or deceleration, and calculates a different symbol depending on whether acceleration or deceleration is identified.

For a contiguous input time-series pair, i.e., a FHR-UP signal pair denoted $\{y, u\}$, with length of $Tf_s$ samples, with $f_s$ as the sampling frequency, feature sequences are made amenable to analysis using generative models (GMs) by first partitioning both y and u into synchronized segments of length $tf_s$ samples, with no overlap. For each segment, indexed by j, a discretization module assigns a feature value $x_j$ using an $H_x$-sized feature value alphabet, based on the following steps.

As a first step, the normalized FHR variability of the $j^{th}$ segment is allowed to be denoted by $v_j$, where $v_j \in [0,1]$. If this segment is not classified as an acceleration or deceleration, then discretization is performed to a label $\xi_j$ according to Equation 3:

$$\xi_j = \begin{cases} 1, & v_j \in [0, b), \\ 2, & v_j \in [b, 2b), \\ \ldots \\ H_v, & v_j \in [1-b, 1], \end{cases} \quad (3)$$

with $b=1/H_v$ as a bin width controlling discretization granularity.

Following the above step, if segment j has at least 50% of samples classified as part of an acceleration, the label $\xi_j$ takes a value depending on acceleration type, with values quantified as $\xi_j=H_v+1$ (normal), $\xi_j=H_v+2$ (prolonged) or $\xi_j=H_v+3$ (baseline change). Thus, $H_A=3$.

If segment j has at least 50% of samples classified as part of a deceleration, the label $\xi_j$ is a value depending on deceleration type, with: $\xi_j=H_v+H_A+1$ (early), $\xi_j=H_v+H_A+2$ (late), $\xi_j=H_v+H_A+3$ (variable) or $\xi_j=H_v+H_A+5$ (baseline change). Thus, $H_D=5$.

A final feature value $x_j$ is assigned. If segment j of the UP signal u has at least 50% of samples classified as part of a contraction, then the feature $x_j=\xi_j+H_v+H_A+H_D$; otherwise, $x_j=\xi_j$. Therefore, $H_x=2(H_v+H_A+H_D)$.

Two important parameters are thereby provided for control of the size of feature-symbol-sequence size and feature resolution, i.e., segmentation period t and bin width b. Available information from both FHR and UP signals is combined into a single discrete feature value.

Figure 2:
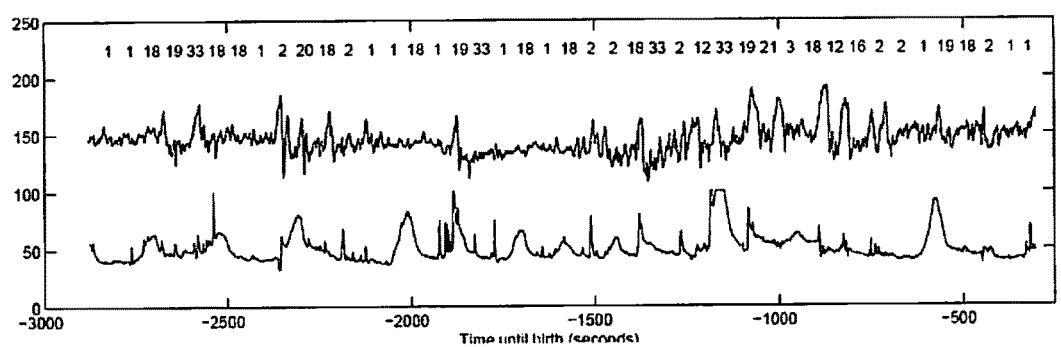
FIG. 2 is a feature sequence chart showing symbol numbers along the top thereof, and FHR and UP signals as the upper and bottom graphs, respectively, according to an embodiment of the present invention.

FIG. 2 is a feature sequence chart showing symbol numbers, FHR, and UP in the top, center and bottom rows, respectively. FIG. 2 provides an example of a feature sequence that, unlike conventional FHR feature extraction methods, e.g., rule-based systems which also consider the baseline FHR as a feature, the restriction of one label per segment forces a choice between the baseline FHR value and variability for all segments not classified as acceleration/deceleration episodes. In FIG. 2, a feature sequence is displayed as a row of symbol numbers at the top thereof, extracted from an FHR, with feature value alphabet $H_x$ size of thirty-four and segment length of t=60 seconds, FHR in bpm, and UP scaled to percentage values.

In a preferred embodiment, FHR variability is utilized instead of baseline to more accurately determine fetal health, with the feature sequence from an $i^{th}$ FHR record denoted as $x_i=\{x_{i,1}, \ldots, x_{i,di}\}$, with the second subscript identifying the segment, and $d_i$ as a total number of segments in the ith record. Feature sequences calculator 140 performs a feature sequence likelihood calculation based on the feature discretization models, with the feature sequences using GMs.

Feature sequence likelihood calculator 140 utilizes parameter learning parameters input from parameter learning module 130, which includes a memory for storing training feature sequences, which are divided into category-specific groups. Parameter learning module 130 uses a training database to learn probabilistic models for each possible fetal category, e.g., healthy and unhealthy. For each newly obtained FHR-UP record, a calculation is performed of a likelihood that the record came from a learnt model, and likelihoods are compared to decide which model is most probable, to provide an output of a corresponding fetal category as a final classifier decision.

For each divided category-specific group in the training database, a count is obtained for all occurring symbols, and a count is obtained for all symbol transitions. Using the obtained count of all occurring symbols, estimation is performed for a memory-less feature alphabet model and a pmf is output for each category. Using the obtained count of all symbol transitions, an estimate is performed of first order Markov chain parameters for a feature-alphabet model, and a feature-symbol transition matrix is output for each category. Using the obtained count of all symbols in the first segments of the training records, a pmf for initial segment symbols output for each category. A decision output, based on the feature sequence likelihood calculation performed by the feature sequence calculator 140, indicates variation in fetal health and is output on display 150.

During monitoring, a plurality of FHR-UP signal pairs are obtained from FHR and UP signals received at each interval of a plurality of intervals during a monitoring period. A feature value is extracted from a finite sized alphabet of feature values for each FHR-UP signal pair, with the size of the alphabet of feature values determined by varying bin width and segmentation period. The extracted feature value is based on a variation of a previous FHR-UP signal pair, and the extracted feature value describes a time dynamic of the FHR-UP signal pair, with the time dynamic including a change in UP contractions, FHR accelerations, FHR decelerations and FHR baseline-variability. In addition, the variation includes UP contraction, FHR acceleration, FHR deceleration and FHR baseline-variability.

The plurality of FHR-UP signal pairs are replaced with a feature value sequence for each FHR-UP signal pair, with the sequences of feature values indicating morphological changes. The feature value sequence is compared with a plurality of possibly previously obtained feature value sequences, the feature value sequence is classified using a generative model and, based on the comparison, an indication is output of health of a fetus from which the FHR signals are obtained, with the fetus being within a uterus associated with the obtained UP signal, and parameter learning is performed to update a database of probabilistic models of possible fetal health.

An apparatus is provided that monitors fetal health, the apparatus including a controller that receives a FHR signal from a heart rate monitor at each interval of a plurality of intervals during a monitoring period, receives the UP signal at each interval of the plurality of intervals, obtains a plurality of FHR-UP signal pairs, and extracts feature values for each FHR-UP signal pair, with the feature values being extracted from a finite sized alphabet of feature values. The controller also outputs an indication of fetus health based on a comparison of the feature value sequence and a plurality of possibly previously obtained feature value sequences, and performs parameter learning to update a database of probabilistic models of possible fetal health.

In the preferred aspects, the apparatus and method are provided to indicate variations in fetal health, with a system that includes a processor configured to execute the above described method. The methods of the preferred aspects are implemented in systems that use software run on a computer processor to carry out the above described methods. While in preferred embodiments, the methods are carried out in an automated format, entirely within the computer processor, it should be understood that one or more components may be carried out by a human and that the methods may involve human interaction or intervention at one or more points.

The computer processor for conducting aspects of the methods of the present invention may be housed in devices that include desktop computers, scientific instruments, hand-held devices, personal digital assistants, phones, a non-transitory computer readable medium, and the like. The methods need not be carried out on a single processor. For example, one or more steps may be conducted on a first processor, while other steps are conducted on a second processor. The processors may be located in the same physical space or may be located distantly. In certain embodiments, multiple processors are linked over an electronic communications network, such as the Internet. Preferred embodiments include processors associated with a display device for showing the results of the methods to a user or users, outputting results as a video image that includes feeder outlines or motifs. The processors may be directly or indirectly associated with information databases. As used herein, the terms processor, central processing unit, and CPU are used interchangeably and refer to a device that is able to read a program from a computer memory, e.g., ROM or other computer memory, and perform a set of steps according to the program. The terms computer memory and computer memory device refer to any storage media readable by a computer processor. Examples of computer memory include, but are not limited to, RAM, ROM, computer chips, digital video discs, compact discs, hard disk drives and magnetic tape. Also, computer readable medium refers to any device or system for storing and providing information, e.g., data and instructions, to a computer processor, DVDs, CDs, hard disk drives, magnetic tape and servers for streaming media over networks. As used herein, encode refers to the process of converting one type of information or signal into a different type of information or signal to, for example, facilitate the transmission and/or interpretability of the information or signal. For example, image files can be converted into, i.e., encoded into, electrical or digital information.

While the invention has been shown and described with reference to certain aspects thereof, it will be understood by those skilled in the art that various changes in form and details may be made therein without departing from the spirit and scope of the present invention as defined by the appended claims and equivalents thereof.

What is claimed:

1. A method for operating an electronic device, the method comprising:
   inputting, to a processor of the electronic device, a fetal heart rate (FHR);
   inputting, to the processor, a plurality of uterine pressure (UP) values corresponding to the input FHR;
   removing, by the processor, artifacts from the FHR and interpolating segments of the FHR;
   storing, by a feature extractor, time information of segments of the interpolated FHR segments;
   searching sub-segments of the stored time information to detect variability of the FHR;
   detecting excess noise in the searched sub-segments;
   obtaining a reduced noise FHR signal by removing sub-segments with detected excess noise;
   detecting a plurality of sub-segments of the reduced noise FHR signal corresponding to an average heart rate baseline;
   detecting at least two sub-segments of the plurality of sub-segments of the reduced noise FHR signal corresponding to contractions based the input plurality of UP values;
   indexing each sub-segment of the detected at least two sub-segments, wherein the indexing comprises assigning a respective feature value to each sub-segment of the detected at least two sub-segments; and
   outputting, to a display of the electronic device, a sequence of symbols of the respective feature value assigned to each sub-segment.

2. The method of claim 1, further comprising detecting that the plurality of sub-segments of the reduced noise FHR signal is free of periods with episodic deviations based on the average heart rate baseline.

3. The method of claim 1, wherein the average heart rate baseline is an average heart rate free from episodic deviations.

4. The method of claim 1, further comprising mapping each indexed sub-segment.

5. The method of claim 1, wherein each symbol of the sequence of symbols is one of $H_x$ values.

6. An electronic device for monitoring fetal health, the device comprising:
   a processor configured to receive a fetal heart rate (FHR) and a plurality of uterine pressure (UP) values corresponding to the input FHR, and remove artifacts from the FHR and interpolate segments of the FHR;
   a feature extractor configured to store time information of segments of the interpolated FHR segments; and
   a display,
   wherein the processor is further configured to control
      searching sub-segments of the stored time information to detect variability of the FHR,
      detecting excess noise in the searched sub-segments,
      obtaining a reduced noise FHR signal by removing the sub-segments with detected excess noise,
      detecting a plurality of sub-segments of the reduced noise FHR signal corresponding to an average heart rate baseline,
      detecting at least two sub-segments of the plurality of sub-segments of the reduced noise FHR signal corresponding to contractions based the input plurality of UP values,
      indexing each sub-segment of the detected at least two sub-segments, wherein the indexing comprises assigning a respective feature value to each sub-segment of the detected at least two sub-segments, and
      displaying, by the display, of a sequence of symbols of respective feature values assigned to each sub-segment.

7. The device of claim 6, wherein the processor is further configured to control detecting that the plurality of sub-segments of the reduced noise FHR signal is free of periods with episodic deviations based on the average heart rate baseline.

8. The device of claim 6, wherein the processor is further configured to control detecting that the average heart rate baseline is an average heart rate free from episodic deviations.

9. The device of claim 6, wherein the processor is further configured to control mapping each indexed sub-segment.

10. The device of claim 6, wherein each symbol of the sequence of symbols is one of $H_x$ values.

* * * * *